(12) United States Patent
Hettler et al.

(10) Patent No.: US 11,344,212 B2
(45) Date of Patent: May 31, 2022

(54) ELECTRONIC DEVICE THAT CAN BE WORN ON THE BODY AND METHOD FOR PRODUCING SAME

(71) Applicant: Schott AG, Mainz (DE)

(72) Inventors: Robert Hettler, Kumhausen (DE); Wee Kiat Chai, Singapore (SG); Rainer Graf, Landshut (DE); Helena Blümel, Frontenhausen (DE)

(73) Assignee: Schott AG, Mainz (DE)

( * ) Notice: Subject to any disclaimer, the term of this patent is extended or adjusted under 35 U.S.C. 154(b) by 0 days.

(21) Appl. No.: 17/313,690

(22) Filed: May 6, 2021

(65) Prior Publication Data

US 2021/0269358 A1 Sep. 2, 2021

Related U.S. Application Data

(63) Continuation of application No. PCT/EP2019/080121, filed on Nov. 4, 2019.

(30) Foreign Application Priority Data

Nov. 6, 2018 (DE) .................. 10 2018 127 619.2

(51) Int. Cl.
*A61B 5/024* (2006.01)
*A61B 5/00* (2006.01)
(Continued)

(52) U.S. Cl.
CPC .......... *A61B 5/02427* (2013.01); *A61B 5/681* (2013.01); *A61B 5/6847* (2013.01);
(Continued)

(58) Field of Classification Search
CPC ... C03C 27/044; A61B 5/681; A61B 5/02416; C03B 23/20
See application file for complete search history.

(56) References Cited

U.S. PATENT DOCUMENTS

| | | | |
|---|---|---|---|
| 2014/0275854 A1* | 9/2014 | Venkatraman | A61B 5/318 600/301 |
| 2015/0282713 A1* | 10/2015 | Fei | A61B 5/681 600/476 |

(Continued)

FOREIGN PATENT DOCUMENTS

| | | |
|---|---|---|
| CN | 105266773 A | 1/2016 |
| DE | 10 2018 127 619 B4 | 10/2020 |

(Continued)

OTHER PUBLICATIONS

Notification of Transmittal of Translation of the International Preliminary Report on Patentability dated May 20, 2021 for International Patent Application No. PCT/EP2019/080121 (8 pages).

(Continued)

*Primary Examiner* — Catherine M Voorhees
*Assistant Examiner* — Roland Dinga
(74) *Attorney, Agent, or Firm* — Taylor IP, P.C.

(57) ABSTRACT

An electronic device is provided which can be worn on the body or implanted into the body, such as in the form of a pulse watch and/or a smartwatch and/or an implant. The electronic device includes a photoplethysmographic measuring device. A transmitter diode and a receiver diode are arranged under a window made of glass or glass ceramics. The window is implemented as a compression glass seal and/or as a fiber-optic plate.

17 Claims, 8 Drawing Sheets

(51) Int. Cl.

| | |
|---|---|
| *C03C 27/04* | (2006.01) |
| *G04G 21/02* | (2010.01) |
| *H01L 31/0203* | (2014.01) |
| *H01L 31/0216* | (2014.01) |
| *H01L 31/0232* | (2014.01) |
| *H01L 31/173* | (2006.01) |
| *H01L 31/18* | (2006.01) |
| *C03B 23/20* | (2006.01) |
| *G04F 13/02* | (2006.01) |
| *G02B 6/42* | (2006.01) |
| *G04B 39/02* | (2006.01) |
| *G02B 6/08* | (2006.01) |

(52) U.S. Cl.
CPC ............ *C03B 23/20* (2013.01); *C03C 27/044* (2013.01); *G02B 6/4203* (2013.01); *G04B 39/02* (2013.01); *G04F 13/02* (2013.01); *G04G 21/025* (2013.01); *H01L 31/0203* (2013.01); *H01L 31/02162* (2013.01); *H01L 31/02325* (2013.01); *H01L 31/173* (2013.01); *H01L 31/18* (2013.01); *A61B 5/02416* (2013.01); *A61B 2562/16* (2013.01); *G02B 6/08* (2013.01)

(56) References Cited

U.S. PATENT DOCUMENTS

| | | | | |
|---|---|---|---|---|
| 2016/0058309 | A1* | 3/2016 | Han | ..................... A61B 5/0261 600/479 |
| 2016/0378069 | A1 | 12/2016 | Rothkopf | |
| 2017/0082433 | A1 | 3/2017 | Huo et al. | |
| 2018/0014781 | A1* | 1/2018 | Clavelle | ................. A61B 5/681 |
| 2018/0042554 | A1 | 2/2018 | Wagner et al. | |

FOREIGN PATENT DOCUMENTS

| | | |
|---|---|---|
| WO | 2015/102589 A1 | 7/2015 |
| WO | 2016/032682 A1 | 3/2016 |
| WO | 2016/071754 A1 | 5/2016 |

OTHER PUBLICATIONS

Notification of the Transmission of the International Search Report and Written Opinion of the International Search Authority or Declaration dated Feb. 10, 2020 for International Application No. PCT/EP2019/080121 (13 pages).

Machine English translation of Notification of the Transmission of the International Search Report and Written Opinion of the International Search Authority or Declaration dated Feb. 10, 2020 for International Application No. PCT/EP2019/080121 (14 pages).

"Extremely small, highly reliable: SCHOTT Primoceler Oy enables next-generation medical implants", SCHOTT, Sep. 5, 2018, Mainz, Federal Republic of Germany (4 pages).

Machine English translation of "Extremely small, highly reliable: SCHOTT Primoceler Oy enables next-generation medical implants", SCHOTT, Sep. 5, 2018, Mainz, Federal Republic of Germany (4 pages).

* cited by examiner

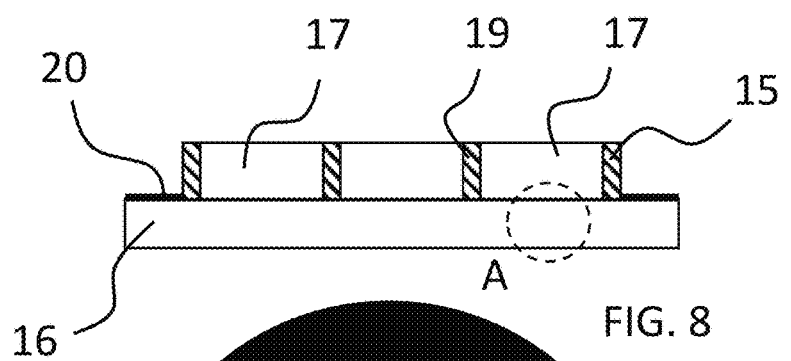
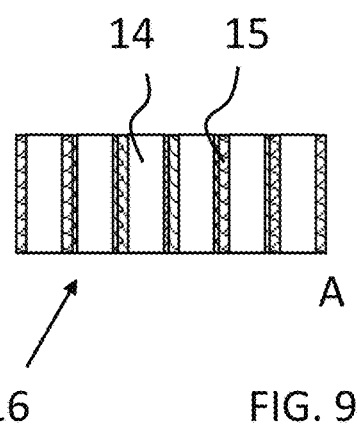
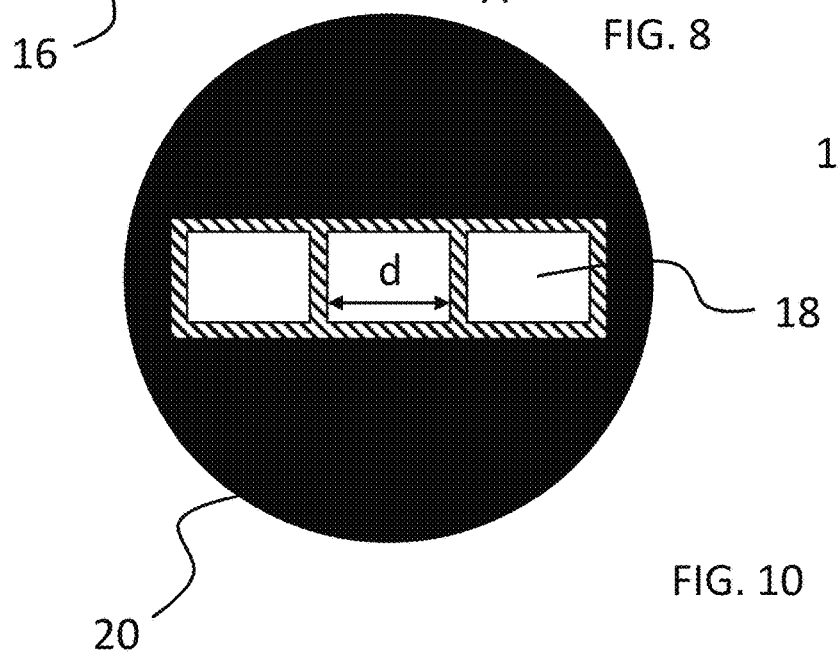
FIG. 8
FIG. 9
FIG. 10

ELECTRONIC DEVICE THAT CAN BE WORN ON THE BODY AND METHOD FOR PRODUCING SAME

CROSS REFERENCE TO RELATED APPLICATIONS

This is a continuation of International Patent Application No. PCT/EP2019/080121 filed on Nov. 4, 2019, which claims priority to German Patent Application No. 10 2018 127 619.2 filed on Nov. 6, 2018, which are incorporated in their entirety herein by reference.

BACKGROUND OF THE INVENTION

1. Field of the Invention

The invention relates to an electronic device that can be worn on or introduced into the body, and to a method for producing such a device. More particularly, the invention relates to a pulse watch and/or a smartwatch and/or a probe and/or an implant comprising a photoplethysmographic measuring device.

2. Description of the Related Art

Electronic devices that can be worn on the body with the back of the device in contact with the skin of the user are known.

In particular so-called pulse watches are known, i.e. electronic devices that include a measuring device for the pulse, i.e. heart rate. Modern pulse watches are usually multifunctional and not only have a heart rate measuring device, but also components for a number of other functions. Such watches may in particular comprise a display, a GPS module, etc. Such watches are also referred to as smartwatches.

The first measuring devices in the form of pulse watches that were available on the market worked according to the electrocardiographic measuring principle. This measuring principle has the advantage that it allows for a very precise measurement.

However, a drawback of the electrocardiographic measuring principle is the usually high energy consumption thereof. Also, the provision of an electrocardiographic measuring device in a smartwatch is complex.

Therefore, in particular the photoplethysmographic measuring principle has established itself as a common measuring principle in smartwatches.

A pulse watch that works according to this measuring principle is disclosed in patent application WO 2015/102589 A1, for example.

The photoplethysmographic measuring principle can be integrated at low cost and so as to use little installation space, for example in the back of a pulse watch.

The measuring principle exploits the fact that the absorption of light, in particular the absorption of certain wavelengths, is a function of hemoglobin concentration in the blood.

Absorption increases with increasing hemoglobin concentration. Thus, the pulse can be determined on the basis of the time profile of light absorption.

For this purpose, photoplethysmographic measuring devices use a transmitter diode, in particular an LED, and a receiver diode, i.e. in particular a photodiode, which is used to measure the back-reflected light. Usually, wavelengths from 510 to 920 nm are used. Green light is particularly suitable for a photoplethysmographic measuring system. Some systems also use light in the IR wavelength range or measure with both infrared and visible light.

A problem is that only a small proportion of the light emitted by the transmitter diode is scattered back.

Furthermore, the variation in absorption as caused by the constantly changing hemoglobin concentration is small.

Moreover, strong optical noise is generated in measuring devices known from practice, caused by ambient light, by artifacts when the user moves, and by a varying distance between the skin and the measuring device, which exacerbates pulse sensing using a photoplethysmographic measuring technique.

What is crucial in this context is the optical quality of the window through which the light exits the pulse watch and/or smartwatch and through which the receiver diode measures the intensity of the reflected light.

In addition to the high optical quality, another requirement for the window is to be made as robust and fluid-tight as possible.

At the same time, if the window is damaged or destroyed, the risk of injury to the user should be kept as low as possible.

SUMMARY OF THE INVENTION

Exemplary embodiments provided according to the invention are based on meeting the aforementioned requirements. The requirements applicable to the pulse watch and/or smartwatch can advantageously also be transferred to probes and/or implants that can be introduced into the human or animal body, including temporarily introduced probes that pass through the body. It is intended to provide a pulse watch and/or smartwatch and/or an implant in which the window for the transmitter and/or receiver diodes is hermetically sealed and in which optical noise as caused by the window is reduced compared to measuring devices known from the prior art, and in which the risk of injury to the user is reduced should the window break.

In some exemplary embodiments provided according to the invention, an electronic device that can be worn on the body or introduced into the body includes: a casing having a top and a bottom; an inorganic support; and at least one window made of at least one of glass or glass ceramics provided on the bottom. The at least one window is fused into the inorganic support and the at least one window is in the form of a compression glass seal.

In some exemplary embodiments provided according to the invention, a method for producing an electronic device is provided. The electronic device includes a casing having a top and a bottom, an inorganic support, and at least one window made of at least one of glass or glass ceramics provided on the bottom, the at least one window being fused into the inorganic support and being in the form of a compression glass seal. The method includes: fusing the at least one window into the inorganic support; and joining the inorganic support to the casing of the electronic device.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIGS. 8 to 10 illustrate the implementation of a window in the form of a fiber-optic plate;

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figures 1, 2:
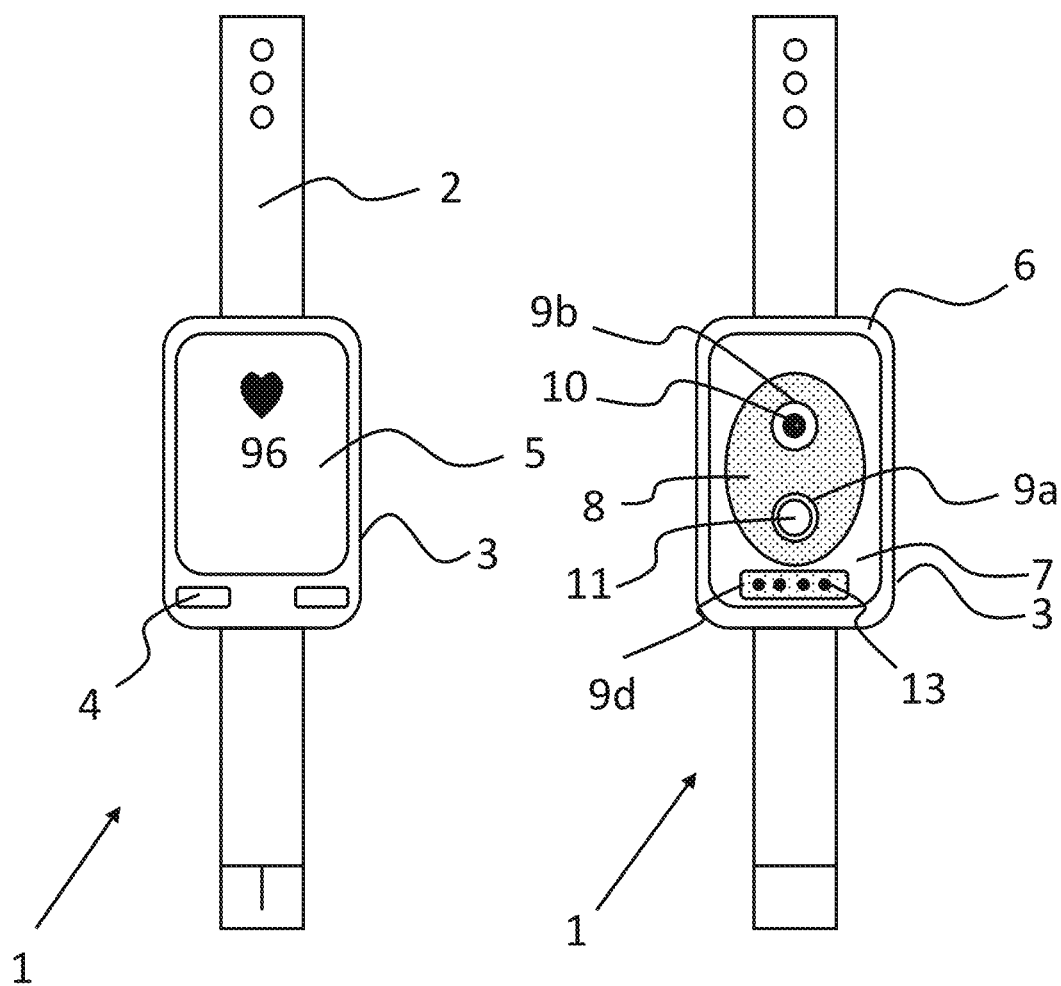
FIG. 1 a schematic view of a front side an exemplary embodiment of an electronic device provided according to the invention in the form of a pulse watch wearable on the body.
FIG. 2 is a schematic view of a back of the electronic device of FIG. 1.

Exemplary embodiments provided according to the invention provide an electronic device that can be worn on or introduced into the body.

The invention relates to an electronic device that can be worn on or introduced into the body, the device being in the form of a pulse watch and/or a smartwatch and/or a probe and/or an implant.

Such an electronic device comprises a casing having a top and a bottom.

The bottom is designed to rests on the user's skin when worn.

According to the invention, at least one window made of glass and/or glass ceramics is provided on the bottom and is fused into an inorganic support.

According to an exemplary embodiment, this window is in the form of a fiber-optic plate.

A fiber-optic plate consists of a large number of individual fibers that extend transversely, such as perpendicular to the top or bottom and which are surrounded by a sheathing material (also referred to as cladding).

Due to the lower refractive index of the cladding material compared to the material of the fibers, total internal reflection is caused so that individual light guides are defined.

Thus, the light is injected into the fibers on one side and re-emerges from the respective same fiber on the other side of the fiber-optic plate.

Optical crosstalk as caused by volume scattering within the window can largely avoided in this way.

The use of a fiber-optic plate may furthermore have the advantage that the optical noise does not or virtually not increase with increasing thickness of the window, since optical crosstalk is virtually absent within the fiber plate.

The fiber-optic plate can therefore be made thicker and thus more stable than in the prior art.

As mentioned previously, the window in the form of a fiber-optic plate may be implemented as a compression glass seal.

The inorganic support may comprise at least one material selected from metal, glass ceramics, and/or opaque glass (at least for the wavelength of the light emitted by the transmitter diode).

In some embodiments provided according to the invention, the support is made at least partially of ceramics or comprises ceramics.

In some embodiments, the electronic device that can be worn on or introduced into the body only has a single window in the form of a fiber-optic plate, with both a transmitter diode and a receiver diode disposed therebelow. This is possible due to the implementation of the window in the form of a fiber-optic plate, since the use of a fiber-optic plate prevents light emitted by the transmitter diode from being reflected back to the receiver diode thereby increasing optical noise. If no window in the form of a fiber-optic plate is used, it is necessary to provide two windows in the support in order to achieve reduced optical noise, one of which is arranged above the transmitter diode and the other one above the receiver diode.

Exemplary embodiments provided according to the invention are based on the finding that a fused glass window with a material bond directly between the material of the support and the glass allows to provide a robust, hermetically sealed bond and at the same time high optical quality of the window.

The window may be made of glass and/or glass ceramics in the form of a compression glass seal.

Such a compression glass seal is provided by using a support with a coefficient of linear thermal expansion α that is greater than that of the glass for the window.

In order to establish a compression glass seal, the window is placed in an opening and is heated together with the support to a temperature above the softening temperature of the glass. Since, during cooling, the material of the support contracts more than the material of the window, the glass is subjected to compressive stress.

Due to this compressive stress state, a particularly tight bond is provided. At the same time, the window per se is also more stable.

It has moreover been found that by providing a compression glass seal, a window can be provided in a form so that craters are caused in the event of damage, such as in the ball drop test. Crater-shaped spalling occurs at the damaged area. The material will spall off in particulate form, especially in powdery form, and so separates from the window.

The ball drop test may be carried out by dropping a steel ball of a predefined mass from a predefined height onto the window under the action of gravity. In the case of windows that have a flat or planar surface, a ball with a mass of 7 g may be used, for convex or concave surfaces, for example, a ball with a mass of 12 g. The drop height for the test of the breaking behavior of the window is 50 cm.

In addition to a more robust design, i.e. a higher force impact at which damage to the window starts to occur in the first place, this also minimizes the risk of injury to the user.

It has been found that the breaking behavior which is favorable for the user, namely that material separated from the window is in powder form, can be achieved if the window has a minimum of surface inaccuracies such as roughness, microdefects and/or shape deviations. There is an interaction of the compression glass seal and the presence of surface structures as manifested in a mean roughness Rq and/or number of microdefects within a measuring section and/or a deviation in shape. These deviations in shape are in particular micro- or nanostructures. It is assumed that these surface structures are effective as starting points for the breaking behavior when the maximum load capacity of the window is exceeded. With the values as specified, sufficient surface structures are present in order to achieve the powdery separated window material that reduces the risk of injury.

One measure for the exemplary surface structures is the root mean square roughness parameter Rq. It is known to a person skilled in the art and is calculated from the root mean square of all ordinate values within a measurement section. The measurement and the parameter are described in DIN EN ISO 4287 (version 2010-07).

Rq values of 2 nm or more may be provided, such as 12 nm or more or 60 nm or more. All of these values can be combined with one another as upper or lower limits. Such Rq values can be achieved by mechanically polishing the fused-in window. This may be advantageous in the case of windows that have a flat or planar surface, such as a surface that is plane-parallel or convex on the side facing the user relative to the surface of the casing.

As an alternative to the roughness and the Rq value, the number of microdefects within a measuring section may be specified as a measure for the surface structures. Exemplary windows are made of glass and/or glass ceramics, which have between 3 and less than 16 microdefects in a measuring section of 10 mm length, such as between 16 and less than 80 microdefects, or between 80 and less than 400 microdefects within this measuring section. This specification is useful for the aforementioned windows with a flat or planar surface, but may also be applied to windows having a curved surface.

Another option for processing the windows and producing the specified surface structures is fire polishing of the windows. In some embodiments, the latter have a fire-polished surface. However, the fire polishing is restricted locally, such as to the surface of the window, such that the compression glass seal is retained. In this way, the windows may have surface structures in the form of a waviness, which may be in a range from 100 nm to 5 µm.

Fire polishing may be advantageous in the case of curved surfaces of the windows, for example concave or convex windows.

Windows with such surface structures are able, with regard to their optical properties, to meet the optical requirements for the optical measurement functions of the electronic device, while in cooperation with the compression glass seal ensuring a reduced risk of injury to the user.

In some embodiments, a support material is used which has a coefficient of linear thermal expansion α (at 20° C.) which is greater than the coefficient of linear thermal expansion of the glass or the glass ceramic by at least 2 ppm/K, such as at least 5 ppm/K.

In some embodiments provided according to the invention, the window made of glass and/or glass ceramics is bonded to the support by a glass solder. Such embodiments provided according to the invention can also be used to provide windows with matched expansion coefficient, depending on the application. This allows providing an assembly consisting of support and window with high thermal resistance.

In some embodiments provided according to the invention, at least two windows made of glass and/or glass ceramic are fused into the support. In this case, one or both windows may also be in the form of a fiber-optic plate.

A transmitter diode is disposed below a first window made of glass and/or glass ceramics, and a receiver diode is disposed below a second window made of glass and/or glass ceramics.

The inorganic support may be opaque, at least for the radiation emitted by the transmitter diode.

The use of two windows in combination with an inorganic support minimizes direct crosstalk from the transmitter diode to the receiver diode. The use of one or more fiber plates will additionally reduce the expansion of the light beams on their way from the transmitter diode and/or to the receiver diode.

The inorganic support may be made of metal, ceramic, glass ceramic, and/or an opaque glass (at least for the wavelength of the light emitted by the transmitter diode).

In some embodiments, metals with a coefficient of linear thermal expansion α from 3 to 25 ppm/K (at 20° C.) are considered as metals for the support.

The employed metals may be substantially free of nickel. The material may meet the requirements of DIN EN 1811 (version 2015-10) and/or DIN EN 12472 (version 2009-9).

Suitable materials include stainless steel, titanium, aluminum, and precious metals, and alloys thereof. Furthermore, a nickel-containing material can also be used if it is provided with a coating that prevents diffusion of nickel, for example a gold coating.

Furthermore, stainless steel can also be used as a casing material for the support, such as austenitic nickel-containing stainless steel. This material forms a chromium oxide layer that prevents nickel diffusion.

Ceramics may likewise be used. Usually, these will already be optically opaque. Fused glass forms a mechanically stable and tight bond with ceramics.

Aluminum oxide, zirconium oxide, aluminum nitride, or porcelain may be used as the ceramics.

Furthermore, the support may consist of a glass, such as a glass which is colored so as to be opaque at least in the wavelength range of the radiation emitted by the transmitter diode. A glass doped with an oxide can be used, for example with cobalt oxide, magnesium oxide, or iron oxide.

Suitable window glasses include borosilicate glasses, aluminum borosilicate glasses, and sodium silicate glasses, for example.

The window may exhibit a transmittance of more than 80%, such as of more than 90%, at least for the radiation emitted by the transmitter diode.

The window may have an anti-reflective coating. This allows to further improve the transmittance.

Such high transmittance reduces optical crosstalk.

Furthermore, the glass may be provided with an anti-reflective coating.

For certain applications, such as for measuring devices for monitoring glucose concentration or oxygen saturation which use infrared light, for example, it is also possible to use an infrared-transmitting glass. For this purpose, sapphire glass can be considered, or else, such as if the window is implemented as a compression glass seal, also borosilicate glass or soda lime glass. Biocompatible and/or bioactive glass and/or glass ceramic materials can be used, such as those that are cell compatible and even suppress the growth of cells on the window.

In some embodiments, the support has a projection in the area of the at least one window made of glass or glass ceramics.

Projection refers to a plateau which protrudes from the adjoining bottom. Such a projection can improve the contact between the window and the skin of the user. This also improves measurement accuracy.

The invention furthermore relates to an electronic device that can be worn on the body and has one or more of the features previously described.

The wearable electronic device comprises a casing having a top and a bottom. The bottom is designed so as to contact the user's skin when worn.

A window made of glass or glass ceramics is provided on the bottom, which according to the invention comprises an optical fiber, such as a window in the form of a fiber-optic plate.

A fiber-optic plate consists of a large number of individual fibers that extend transversely, such as perpendicular to the top or bottom and which are surrounded by a sheathing material (also referred to as cladding).

Due to the lower refractive index of the cladding material compared to the material of the fibers, total internal reflection occurs so that individual light guides are defined.

Thus, the light is injected into the fibers on one side and re-emerges from the same respective fiber on the other side of the fiber-optic plate.

Optical crosstalk as caused by volume scattering within the window can largely be avoided in this way.

At the same time, the use of a fiber-optic plate may have the advantage that the optical noise does not or virtually not increase with increasing thickness of the window, since optical crosstalk is virtually absent within the fiber plate.

The fiber-optic plate can therefore be made thicker and thus more stable than in the prior art.

The window consisting of a fiber-optic plate may be implemented in the form of a compression glass seal, as mentioned previously.

In some embodiments, the at least one window made of glass or glass ceramics is in the form of a filter for a receiver diode and/or a transmitter diode.

For this purpose, it is contemplated to provide window(s) that are colored so as to exhibit higher transmittance for the wavelength of the transmitter diode than for other wavelengths.

This allows in a simple way to reduce the optical noise caused by ambient light.

The invention moreover relates to the improvement of the dimensions of a pulse watch and/or smartwatch which comprises at least two windows provided at a back of the device.

The first window made of glass and/or glass ceramics which has the transmitter diode arranged therebelow is spaced apart from the second window made of glass and/or glass ceramic which has the receiver diode arranged therebelow by an edge-to-edge distance s.

The first and/or second windows have a diameter d.

It has been found that the optical signal at the receiver diode is optimized with a ratio s/h between 2 and 7, such as between 3 and 5.

Furthermore, the first window and/or the second window have a height h associated therewith, which corresponds to the thickness of the window.

In some embodiments, s/d is 1 to 3, such as 1.5 to 2.5.

In some embodiments, at least one electrical feedthrough is embedded in the window made of glass.

In some embodiments, the at least one electrical feedthrough is embedded in a separate window made of glass or glass ceramics.

Electrical feedthroughs through the window can be provided by a compression glass seal.

The electrical feedthroughs may, for example, be used to provide power supply for recharging.

Furthermore, an electrical feedthrough may be used to provide a sensor area or to electrically connect a sensor area.

It is contemplated that the sensor area is provided for a measuring device that works according to the electrocardiographic measuring technique, for a temperature measurement or moisture measurement of the skin and/or of media surrounding the probe and/or the implant, such as blood and/or gastric fluid, etc.

A conductivity measurement of the skin and/or of the media surrounding the implant can also be performed using the electrical feedthroughs. This also allows to draw conclusions about the physical condition of the wearer.

Furthermore, electrical feedthroughs can be used to provide an electronic interface.

For example, according to some embodiments it is contemplated for the pulse watch to comprise a photoplethysmographic as well as a electrocardiographic measuring device.

The invention furthermore relates to a support comprising a window made of glass and/or glass ceramics for the bottom of the casing of a device that can be worn on the body as described previously.

The invention also relates to a method for producing an electronic device as described previously, which can be worn on the body.

A window made of glass and/or glass ceramics is integrated into an inorganic support by being fused thereto. The inorganic support is then joined to the casing of the electronic device that can be worn on the body.

A compression glass seal is provided by using a support that has a greater coefficient of linear thermal expansion than the glass for the window.

Referring now to the drawings, FIGS. 1 and 2 are schematic views showing an electronic device that can be worn on the body, in the form of a pulse watch 1.

As illustrated in FIG. 1, pulse watch 1 comprises a casing 3 with a bracelet 2 which allows to attach the pulse watch 1 to the user's arm.

The user can read the pulse, i.e. heart rate, from a display 5 provided on the front side of the casing 3. The pulse watch 1 furthermore comprises operating elements 4, for example in the form of buttons. Also, for operation, the display 5 may be a touch display.

In some embodiments, the pulse watch 1 is a so-called "smartwatch" and thus can serve for a multitude of other functions.

FIG. 2 shows the back 6 of the casing of pulse watch 1. When worn, the back of casing 3 of the pulse watch contacts the user's skin.

In this exemplary embodiment, a support 7 made of metal such as stainless steel is integrated in the back 6 that is made of plastic.

The metallic support 7 has a plateau-like projection 8 in which the windows made of glass 9a, 9b are integrated at a distance from one another. One or both windows 9a, 9b may be in the form of fiber-optic plates.

The windows 9a, 9b are implemented as compression glass seals. A receiver diode 11 is provided below window 9a, and a transmitter diode 10, i.e. an LED, is provided below window 9b.

Transmitter diode 10 and receiver diode 11 form part of a photoplethysmographic measuring device which is used to measure the user's pulse.

Receiver diode 11 is used to measure the intensity profile of the light from transmitter diode 10 returning due to volume scattering in the tissue of the user.

The pulse can be calculated based on the hemoglobin concentration which varies periodically with the pulse. The projection 8 of support 7 ensures improved contact of the windows 9a, 9b with the user's skin surface.

In this exemplary embodiment, the support 7 comprises a further window 9d made of glass and/or glass ceramics, which comprises a plurality of electrical feedthroughs 13. In this exemplary embodiment, the electrical feedthroughs 13 serve to provide terminals for an electronic interface via which the pulse watch 1 can be recharged and via which data can be exchanged, such as in order to install a software.

The metallic support 7 can be joined to the rest of the casing, such as a back 6 of the casing, for example.

The casing of pulse watch 1 may be made of metal. The support 7 may also be implemented in the form of a rear casing half.

With reference to FIGS. 3 to 6, different embodiments of a support will be explained, as can be used for an electronic device provided according to the invention, which comprises at least one window 9.

Figure 3:
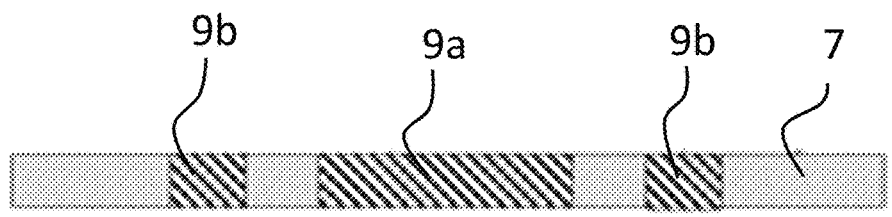
FIGS. 3 to 6 illustrate different exemplary embodiments of a support provided with at least one window, which defines at least part of the bottom of a pulse watch, according to the invention.

In the exemplary embodiment according to FIG. 3, a support 7 is provided which is made of metal, ceramic, or an opaque glass, for example.

Windows 9a and 9b are made of a material that exhibits high transmittance for the light emitted by the transmitter diode and may be in the form of fiber-optic plates.

Support 7, by contrast, may be effective as an optical barrier in order to suppress light from the transmitter diode from being directly transferred to the receiver diode via windows 9a, 9b even more than is the case when using only one window in the form of a fiber-optic plate.

In order to increase optical quality, it is conceivable for windows 9a, 9b to be polished.

Windows 9a and 9b may be provided in the form of compression glass seals.

The implementation as a compression glass seal allows to provide a casing with a helium leak rate of less than $10^{-8}$ mbar·l/s.

In the exemplary embodiment illustrated here, at least two windows 9b are provided, with a transmitter diode arranged below each of them.

The windows 9b for the transmitter diode may be located on either side of the window 9a for the receiver diode.

In this exemplary embodiment, window 9a for the receiver diode is made larger than the windows 9b for the transmitter diodes.

Adjacent to the windows, the support 7 may have a thickness of 0.3 to 2 mm, such as 0.5 to 1 mm.

Windows 9a, 9b may occupy the entire height of the support 7 in the area of the windows 9a, 9b.

Figure 3A:
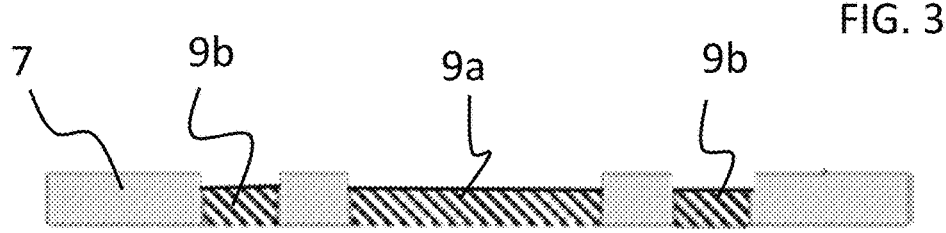

In the exemplary embodiment according to FIG. 3A, the support 7 protrudes beyond the at least one window 9a, 9b made of glass and/or glass ceramics along the edges thereof.

This simplifies the fabrication process in the case of a compression glass seal embodiment. The protruding of support 7 along the edges and the associated countersunk arrangement of window 9a, 9b allows accommodating variations in volume of the glass material of windows 9a, 9b.

It will be understood that the side with the protrusion may be the inner side of the support 7.

Figure 4:
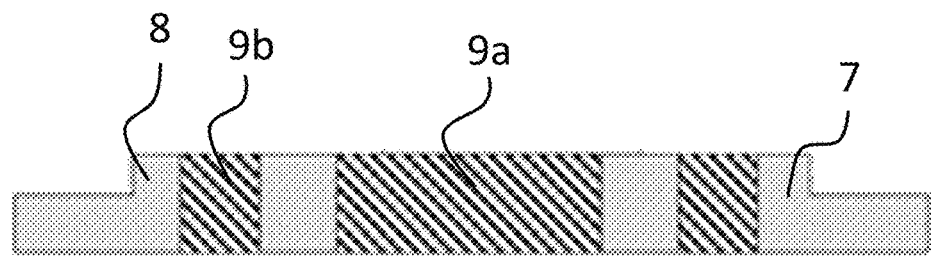

FIG. 4 shows an alternative embodiment in which the support 7 has a projection 8 (as shown in FIGS. 1 and 2 as well). Windows 9a, 9b are provided within the area of the projection 8.

The projection improves the contact of windows 9a, 9b with the user's skin.

Figure 5:
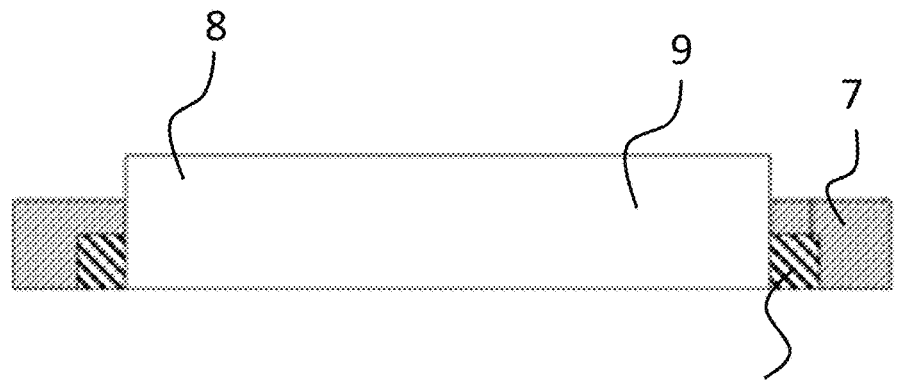

FIG. 5 shows an alternative embodiment provided according to the invention, in which a single window 9 made of glass or glass ceramics is integrated in the support 7, below which both the transmitter diode and the receiver diode are arranged. This single window 9 may be a fiber-optic plate.

In this exemplary embodiment, the window 9 is not implemented as a compression glass seal, but rather is bonded to the support 7 by a glass solder 12.

The glass solder 12 is disposed in an inner groove of the support 7.

In this exemplary embodiment, the window 9 itself defines a projection 8.

Figure 6:
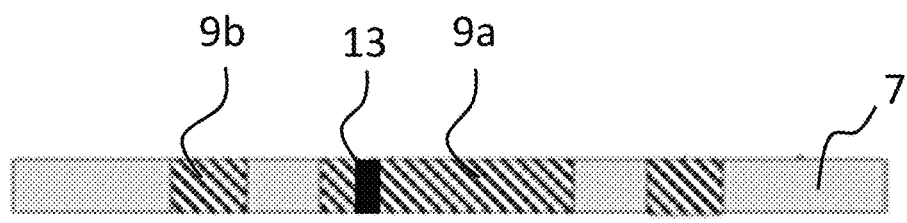

FIG. 6 shows a further exemplary embodiment in which an electrical feedthrough 13 is provided in a window 9a, for example in the form of a pin.

Otherwise, support 7 with windows 9a, 9b corresponds to the exemplary embodiment provided according to FIG. 3.

Glass-sealed electrical feedthroughs 13 are used to provide further functionalities.

For example, electrical feedthrough 13 may serve as a sensor surface for an additionally provided electrocardiographic measuring device of the pulse watch.

Figure 7:
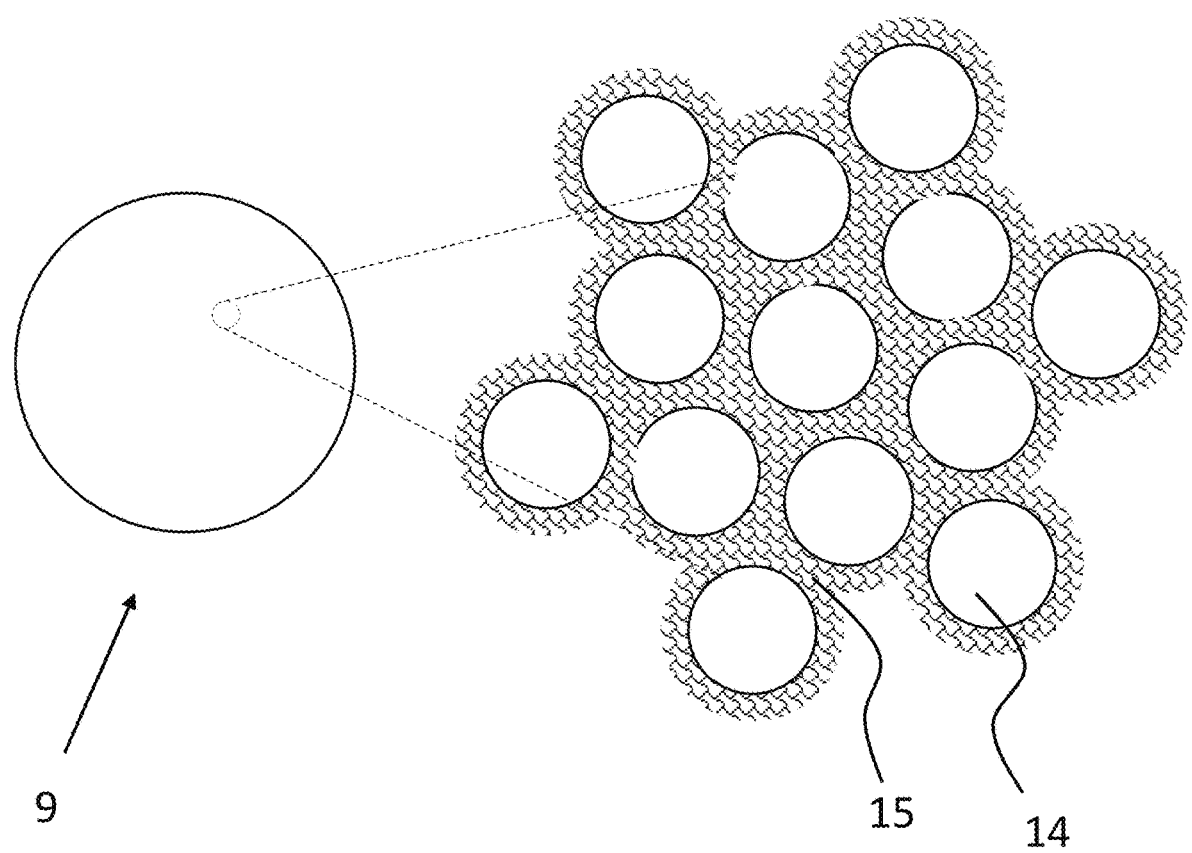
FIG. 7 illustrates an exemplary embodiment of a window, in which the window is in the form of a fiber optic plate.

FIG. 7 illustrates an exemplary embodiment of a window 9, in which the window 9 is in the form of a fiber-optic plate.

Instead of a homogeneous glass material, a fiber-optic plate is made up of fibers 14, such as glass fibers, which are embedded in a cladding material 15 that may also be made of glass, as can be seen in the detailed view on the right.

The cladding material 15 has a lower refractive index than the material of the light-conducting fibers 14.

Thus, total internal reflection occurs at the interface and the light is transmitted within the light-conducting fibers 14 from one end to the other end thereof.

The use of a fiber-optic plate may have the advantage that in the so defined window 9, volume scattering which might otherwise cause direct transfer of light to the receiver diode, is prevented or is very low.

Rather, the light remains within the individual fibers 14.

The thickness of the fiber-optic plate has only little influence on optical noise.

In order to further reduce optical noise, such as to reduce moiré effects, the fiber-optic plate may comprise colored fibers, such as statistically distributed colored fibers.

The fiber-optic plate may be implemented as a compression glass seal as well.

FIG. 8 shows another embodiment that uses a fiber-optic plate 16 that is integrated into a support.

In the sectional view of FIG. 8 it can be seen that the fiber-optic plate 16 is bonded to partition walls 19.

In the assembled state, these walls 19 define chambers 17 on the inner side, in which the transmitter diode and/or photodiode is arranged, for example.

As shown in the plan view of FIG. 10, the fiber plate 16 may be provided with a masking 20 around the transparent areas 18 thus defined, which masking is opaque at least for the wavelength of the transmitter diode.

In the detailed illustration of area A of FIG. 8 it can be seen that the fiber-optic plate 16 consists of a multiplicity of light-conducting fibers 14 which are embedded in a cladding material 15.

Figure 11:
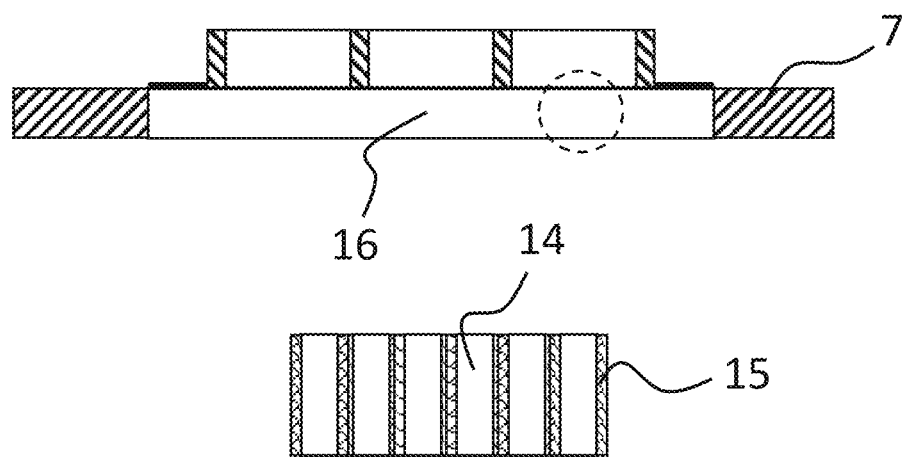
FIGS. 11 and 12 illustrate different exemplary ways of joining a window to a support.

FIG. 11 illustrates, by way of one exemplary embodiment, how the fiber-optic plate 16 is joined to the support 7 which may be made of metal.

In this exemplary embodiment, the fiber-optic plate 16 is implemented as a compression glass seal. That is, the fiber-optic plate 16 has a lower coefficient of linear thermal expansion α than the support 7.

During manufacture, the fiber-optic plate 16 is heated so as to at least reach the softening temperature of the cladding material 15. During cooling, the support 7 contracts more than the fiber-optic plate 16, so that compressive stress is produced in the fiber-optic plate 16.

Figure 12:
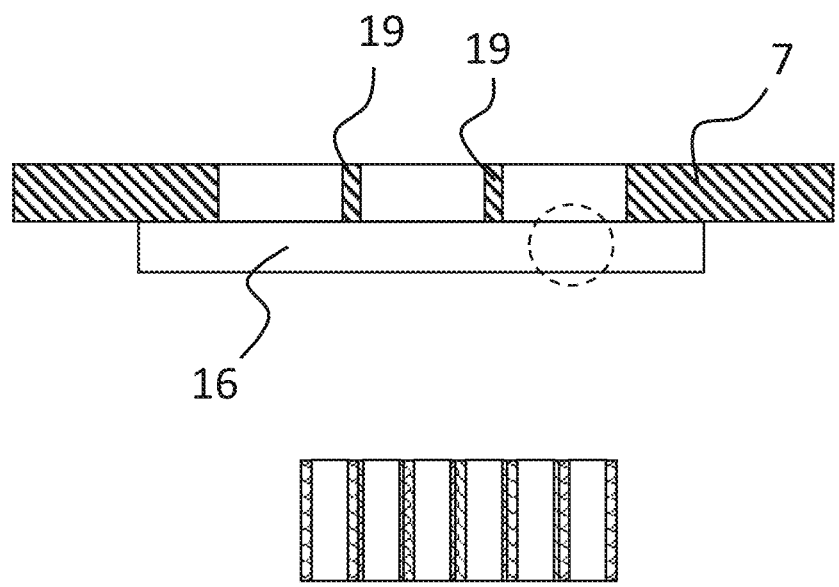

FIG. 12 shows an alternative embodiment in which the fiber-optic plate 16 is attached to one side of the support 7.

The bond may be produced using a glass solder or by anionic bonding, for example.

In this exemplary embodiment, the partition walls 19 are defined by the support 7, which means they are at the same level as the support. The partition walls 19 may be formed by stamping from a support 7 made of metal, for example.

Figure 13:
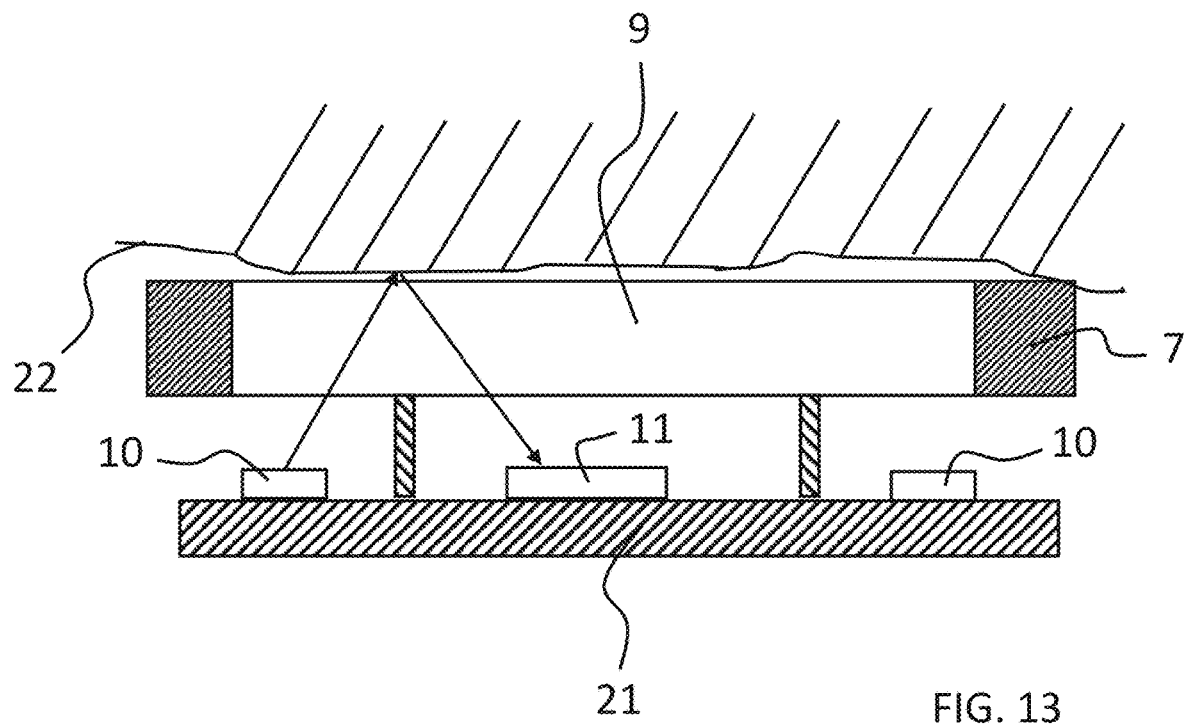
FIG. 13 schematically illustrates a photoplethysmographic measuring device which comprises a single window in the form of a compression glass seal.

With reference to FIG. 13, the operating principle of the photoplethysmographic measuring device shall be explained.

In this exemplary embodiment in which the window 9 is not implemented as a fiber-optic plate, the pulse watch has a casing back comprising a support 7 in which a window 9 made of glass or glass ceramics is integrated.

Light from transmitter diodes 10 that are disposed on a printed circuit board 21 arranged inside the casing is radiated through the window 9 and onto the skin surface 22 of the wearer.

Volume scattering occurs in the tissue surrounding the skin surface 22, and a small proportion of the light incident on the skin surface 22 is scattered back to the receiver diode 11. If the window 9 is in the form of a fiber-optic plate, this proportion can be reduced.

The pulse can be deduced based on the change in intensity as a function of hemoglobin concentration.

In such measuring devices, a large proportion of the signal applied to the receiver diode 11 consists of optical noise.

In order to reduce the optical noise, the window 9 may be implemented as a color filter which transmits light in the wavelength range of the transmitter diode 10, for example.

However, volume scattering may also occur within the window 9, due to inhomogeneities in the glass, which amplify the optical noise. This depends on the optical quality of the window 9 and on the thickness of the window 9, inter alia.

Figure 14:
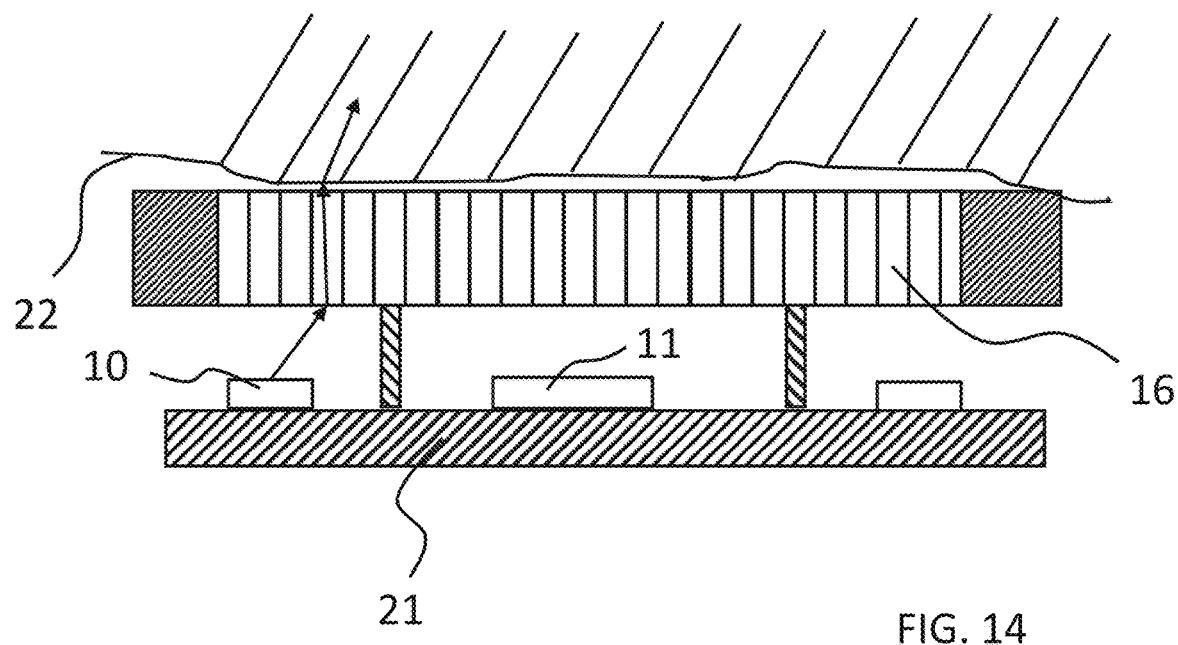
FIG. 14 illustrates a photoplethysmographic measuring device comprising a fiber-optic plate as a window.

FIG. 14 shows that a fiber-optic plate 16 can be used as the window, instead of a conventional window.

When using a fiber-optic plate 16, the light, when injected into the optical fibers, remains within the respective individual light-conducting fibers, so that backscattering of light within the fiber-optic plate 16 onto the receiver diode 11 cannot occur, or at least to a much lesser degree.

Appropriate choice of the refractive index of the fibers and of the cladding allows optimizing the acceptance angle in order to reduce optical noise.

Figure 15:
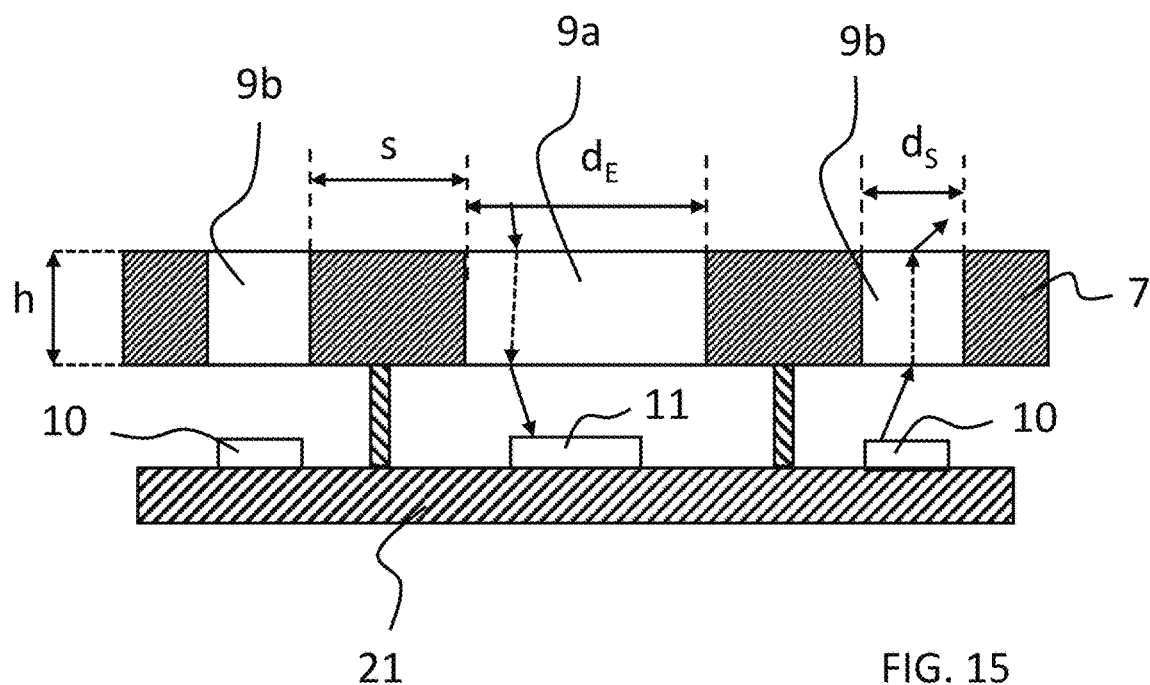
FIGS. 15 and 16 illustrate in more detail the dimensioning of the thickness of the window and the spacing of the windows, with FIG. 15 being a schematic sectional view and FIG. 16 being a contour map based on a simulation, in which the sensor signal is plotted as a function of the thickness of and the spacing between the windows.

With reference to FIG. 15, the influence of the geometry of the window and the support shall be explained.

This exemplary embodiment again illustrates a photoplethysmographic measuring device which comprises the transmitter diodes 10 and the receiver diode 11 which are arranged on a printed circuit board 21.

Windows 9b for the transmitter diodes and window 9a for the receiver diode 11 are integrated in the support 7 of the pulse watch.

For the transmitter diode shown on the right, an exemplary light ray is indicated, which is incident on window 9b.

Part of the light emitted through window 9b is backscattered due to volume scattering in the tissue of the wearer of the pulse watch and is incident on receiver diode 11 through window 9a.

Window 9a of receiver diode 11 has a diameter $d_{Rx}$, and window 9b of the transmitter diode has a diameter $d_{Tx}$.

In the context of the invention, the diameter of windows having a non-circular cross-section refers to the width of a window in the direction towards the other window (cf. "d" in FIG. 10).

The window(s) of transmitter diode 9b is or are spaced apart from window 9a of the receiver diode by an edge-to-edge spacing s.

The windows have a height h corresponding to the thickness of the respective window.

Figure 16:
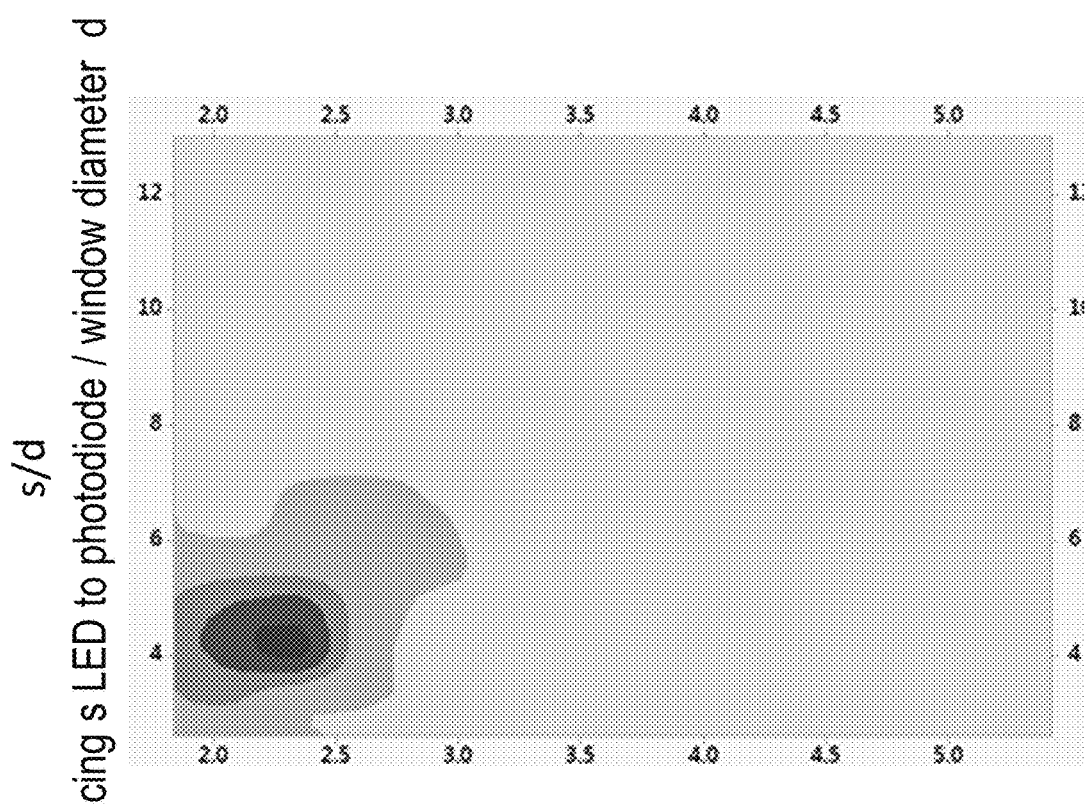

FIG. 16 shows a contour map of a simulation of the optical signal applied to the receiver diode. The darker the area, the better the optical signal.

Plotted on the horizontal axis is the spacing s between the LED and the photodiode divided by the window diameter d ($d_{Rx}$ or $d_{Tx}$).

Plotted on the vertical axis is the spacing s between the LED and the photodiode divided by the thickness h of the window.

It has been found that an optimum signal can be obtained under the following conditions:

s divided by $d_{Rx}$ or $d_{Tx}$ is between 3 and 5;
s divided by h is between 1.5 and 2.5.

Figure 17:
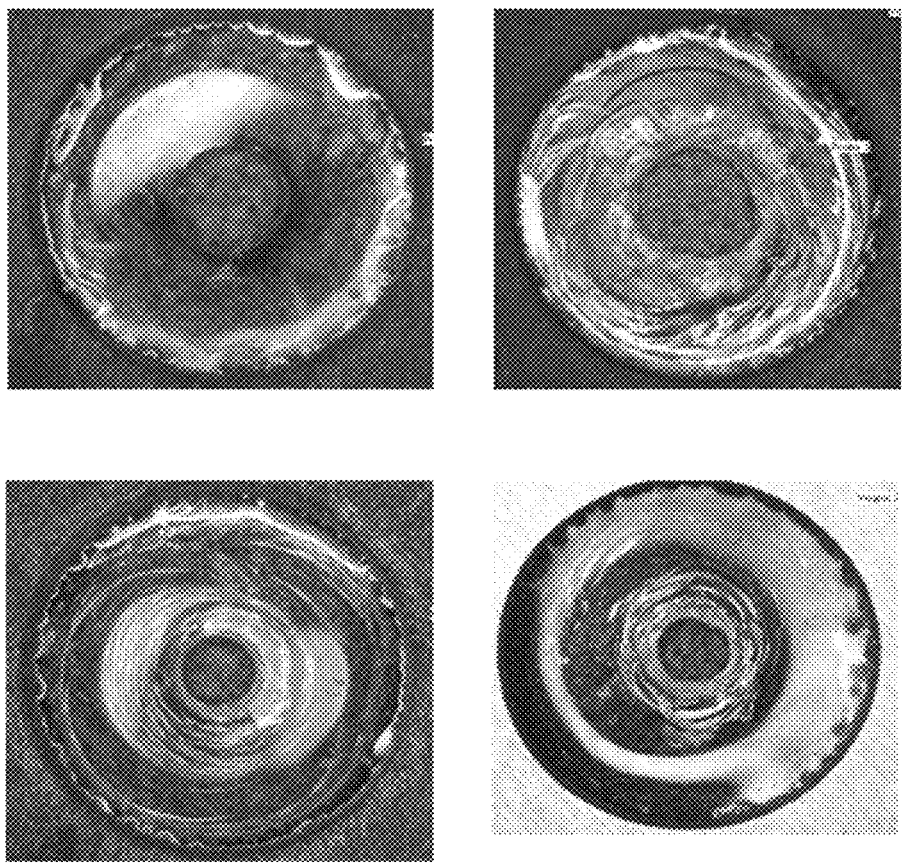
FIG. 17 shows photographs of damage to a window in the form of a compression glass seal as caused by a ball drop test.

FIG. 17 shows photographs taken of a compression glass seal for a pulse watch provided according to the invention after a ball drop test.

In all three photographs it can be seen that crater-like spalling is caused when the window is damaged. Due to the compression glass seal, the material is spalling off or bursting away substantially in the form of powder, i.e. the glass and/or glass ceramic material separated from the window will be powdery. This reduces the risk of injury to the user. At the same time, the compression glass seal reduces the risk of cracking and complete breakage of the window. This means that exemplary embodiments provided according to the invention have the advantage of enhancing the mechanical stability of the window, so that damage will only occurs in the event of greater impacts, and so that in the case of such damage the risk of injury to the user is minimized.

Exemplary embodiments provided according to the invention allowed improving the optical noise in a photoplethysmographic measuring device as well as to increase the stability of a pulse watch.

Figure 18:
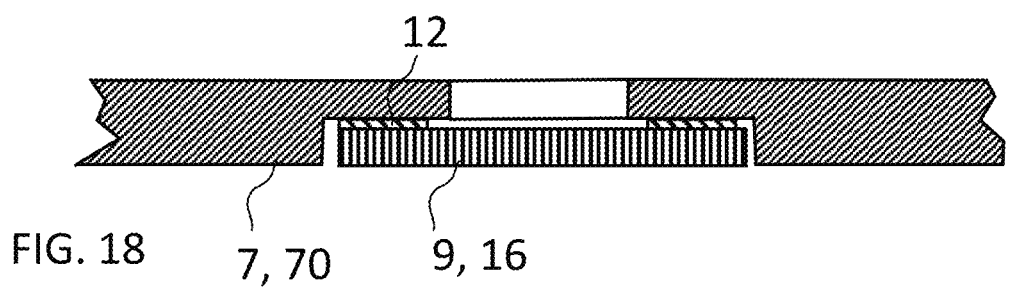
FIG. 18 illustrates a further exemplary embodiment including a ceramic support.

FIG. 18 shows a further exemplary embodiment provided according to the invention. Here, a window 9 in the form of a fiber-optic plate 16 is integrated into a support 7, 70 that is made of ceramics. The window 9 is fixed by a glass solder 12, without compression. Accordingly, more generally, it is contemplated for the window provided according to some embodiments, such as in the form of a fiber-optic plate, to be bonded to a ceramic support 7. The bond between the ceramic support 7 and the window 9 may be a compression glass seal or, as illustrated, a bond via a glass solder 12.

Figure 19:
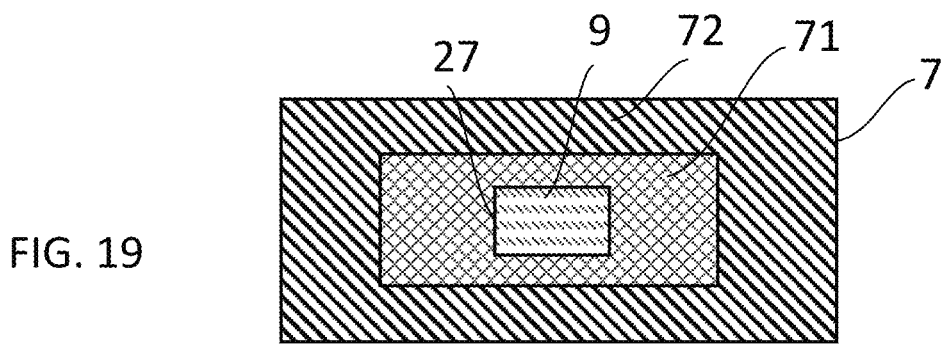
FIG. 19 illustrates an exemplary embodiment of a support in a plan view.

FIG. 19 shows an example of a support 7 that comprises two parts 71, 72, wherein the single opening 27 with window 9 is provided in one of the parts 71, and this part 71 in turn is integrated into a further part 72 so that the further part 72 surrounds like a ring the part 71 having the opening 27. As in the example of FIG. 18, the inner part 71 may be a ceramic component. According to some embodiments, the inner part 71 is made of opaque glass. The outer ring-like surrounding part 72 may be metallic. Without being limited to the specific example, it is contemplated according to some embodiments that a support 7 is provided consisting of two parts 71, 72, including an outer metallic part 72 that surrounds in a ring-like manner an inner part 71 made of ceramics or of opaque glass, and that the opening 27 sealed by the window 9 is provided in the inner part 71.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMERALS

1 Pulse watch
2 Bracelet
3 Casing
4 Operating element
5 Display
6 Back of casing
7 Support
8 Projection
9, 9a, 9b, 9d Window made of glass or glass ceramics
10 Transmitter diode
11 Receiver diode
12 Glass solder
13 Electrical feedthrough
14 Light-conducting window
15 Cladding material
16 Fiber-optic plate
17 Cavity
18 Transparent area
19 Partition wall
20 Masking
21 Printed circuit board
22 Main surface
27 Opening in 7
70 Support 7 made of ceramics
71, 72 Parts of 7

What is claimed is:

1. An electronic device that can be worn on the body or introduced into the body, comprising:
   a casing having a top and a bottom;
   an inorganic support; and
   at least one window made of at least one of glass or glass ceramics provided on the bottom, wherein the at least one window is fused into the inorganic support, wherein the at least one window is in the form of a compression glass seal, wherein the at least one window is a compression glass seal, which is designed such that in the event of damage craters are produced.

2. The electronic device of claim 1, wherein the at least one window comprises at least two windows made of at least one of glass or glass ceramics that are fused into the inorganic support, the at least two windows comprising a first window and a second window, the electronic device further comprising a transmitter diode disposed below the first window and a receiver diode disposed below the second window.

3. The electronic device of claim 2, wherein the first window is spaced apart from the second window by an edge-to-edge spacing s and at least one of the first window or the second window has a diameter d, with a ratio s/d=2 to 7.

4. The electronic device of claim 2, wherein the first window made is spaced apart from the second window by an edge-to-edge spacing s and at least one of the first window or the second window has a height h, with a ratio s/h=1 to 3.

5. The electronic device of claim 2, wherein the inorganic support is opaque for radiation emitted by the transmitter diode.

6. The electronic device of claim 1, wherein the inorganic support comprises at least one of a metal, glass ceramics, or opaque glass.

7. The electronic device of claim 1, wherein the inorganic support has a further window comprising at least one electrical feedthrough.

8. The electronic device of claim 7, wherein the at least one electrical feedthrough serves as a measurement electrode or is connected to a measurement electrode.

9. The electronic device of claim 1, wherein the inorganic support has a projection in an area of the at least one window.

10. The electronic device of claim 1, wherein the at least one window comprises an optical fiber.

11. The electronic device of claim 1, wherein the at least one window is a compression glass seal which is designed such that in the event of damage at least one of glass or glass ceramic material separated from the at least one window is powdery.

12. The electronic device of claim 1, wherein the at least one window is a compression glass seal and has a root mean square roughness value Rq of 2 nm or more.

13. The electronic device of claim 1, wherein the at least one window is a compression glass seal which has from 3 to less than 16 microdefects within a measuring section of 10 mm in length.

14. The electronic device of claim 1, wherein the at least one window is a compression glass seal and has a fire-polished surface on a side facing away from the casing.

15. The electronic device of claim 1, wherein the at least one window is in the form of a filter for at least one of a receiver or a transmitter diode.

16. The electronic device of claim 1, wherein the electronic device is a pulse watch comprising a measuring device operating on the principle of photoplethysmography.

17. A method for producing an electronic device, the electronic device comprising a casing having a top and a bottom, an inorganic support, and at least one window made of at least one of glass or glass ceramics provided on the bottom, the at least one window being fused into the inorganic support and being in the form of a compression glass seal, wherein the at least one window is designed such that in the event of damage craters are produced, the method comprising:
   fusing the at least one window into the inorganic support; and
   joining the inorganic support to the casing of the electronic device.

* * * * *